US011311229B2

(12) United States Patent
Lee et al.

(10) Patent No.: US 11,311,229 B2
(45) Date of Patent: Apr. 26, 2022

(54) MEMBRANE BASED SEMI-DRY ELECTRODE FOR RECORDING ELECTROENCEPHALOGRAM

(71) Applicant: Korea University Research and Business Foundation, Seoul (KR)

(72) Inventors: Seong-Whan Lee, Seoul (KR); Ji-Yong Kim, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 794 days.

(21) Appl. No.: 16/155,945

(22) Filed: Oct. 10, 2018

(65) Prior Publication Data
US 2020/0022605 A1 Jan. 23, 2020

(30) Foreign Application Priority Data
Jul. 20, 2018 (KR) .......................... 10-2018-0085038

(51) Int. Cl.
*A61B 5/291* (2021.01)

(52) U.S. Cl.
CPC ...... *A61B 5/291* (2021.01); *A61B 2562/0217* (2017.08)

(58) Field of Classification Search
CPC ........... A61B 5/291; A61B 5/25; A61B 5/251; A61B 5/266; A61B 5/6814; A61B 5/6829
See application file for complete search history.

(56) References Cited

U.S. PATENT DOCUMENTS

2017/0135596 A1* 5/2017 Fan .................... A61B 5/291

FOREIGN PATENT DOCUMENTS

| JP | 2012161419 A | 8/2012 |
| JP | 2014057642 A | 4/2014 |

\* cited by examiner

*Primary Examiner* — Eun Hwa Kim
(74) *Attorney, Agent, or Firm* — Cantor Colburn LLP

(57) ABSTRACT

A semi-dry electrode for recording an electroencephalogram, includes an outer membrane that forms an electrode contact surface with a predetermined area contacting a scalp; an electrode body that is connected to an edge of the outer membrane and forms an internal space into which an electrolyte solution is filled; and an electrical conductor sensor that is located inside the electrode body and measures an ion current transmitted through the outer membrane. The outer membrane has a plurality of fine holes and holes that are larger than the fine holes.

16 Claims, 11 Drawing Sheets

(a) Flat surface  (b) Swelled surface  (c) Discharging of electrolyte solution by pressure (a)

(b) Impedance after one hour (c) Impedance after five hours (d) Impedance after seven hours (a) Electroencephalogram data at earlier stage of measurement (b) Electroencephalogram data after eight hours

MEMBRANE BASED SEMI-DRY ELECTRODE FOR RECORDING ELECTROENCEPHALOGRAM

CROSS-REFERENCE TO RELATED APPLICATION

This application claims priority to and the benefit of Korean Patent Application No. 10-2018-0085038 filed in the Korean Intellectual Property Office on Jul. 20, 2018, the entire contents of which are incorporated herein by reference.

BACKGROUND (a) Field

The present invention relates to an electrode for recording an electroencephalogram.

(b) Description of Related Art

An electroencephalogram recording method includes a non-invasive technique for attaching electrodes to a scalp and recording brain signals. Representative electrode techniques used here include using a wet electrode and a dry electrode.

The wet electrode uses an electrolyte gel between a scalp and an electrode, and it has a merit of reducing contact impedance of the scalp and the electrode to 1-10 kΩ by the electrolyte gel. However, it takes 30 minutes to one hour of an electrode setup time to insert the electrolyte gel between the scalp and the electrode. The electrolyte gel attached to the scalp and hair makes user inconvenient. As the electrolyte gel dries, impedance increases to worsen electroencephalogram recording efficiency.

To improve the user inconvenience caused by the electrolyte gel, a dry electrode technique has been introduced. The dry electrode is manufactured with an electrical conductor material with high conductivity, so there is no need to use the electrolyte gel. Therefore, in the case of recording an electroencephalogram based on the dry electrode, there are merits of allowing a short electrode setup time and generating no scalp defilement by the electrolyte gel. However, the dry electrode has very high contact impedance (about 80 kΩ) compared to the wet electrode. Electroencephalogram signal includes much noise, so electroencephalogram recording reliability is low. Particularly, it is difficult to completely attach the dry electrode to the scalp. When the user moves, the electrode may be easily shaken, so it is weak in noise. An electrode cap attached the electrodes makes the electrode to the scalp closely and reduce the contact impedance. However, the electrode cap makes user inconvenient.

A semi-dry electrode technique has been researched as a new type electrode for recording an electroencephalogram. The semi-dry electrode stores an electrolyte solution inside the electrode, and does not need to use the electrolyte gel. The semi-dry electrode is a hybrid electrode for solving the drawbacks of the wet electrode and the dry electrode and obtaining the merits of the wet electrode and the dry electrode. That is, the semi-dry electrode uses no electrolyte gel, so the merits that the electrode setup time is short, defilement of the scalp is rare, and the contact impedance is lower than the dry electrode are provided. However, prior semi-dry electrode has the following limitations.

First, the contact impedance of the prior semi-dry electrode is 30-80 kΩ, which is higher than that of the wet electrode, so it is substantially influenced by noise and the signal is distorted.

Second, the prior semi-dry electrode is manufactured with materials lacking flexibility such as titanium (Ti), a polymer, ceramic, silicon, or polyurethane, so it is difficult to freely transform it. Therefore, it is difficult to completely closely attach the semi-dry electrode to the scalp at a curved area. To improve this problem, some prior semi-dry electrodes were introduced in which the electrode contact side is manufactured with a plurality of pins or a felt pen shape. Even though a thin and sharp electrode shape passes through hair, it is difficult for the electrode contact side to balance itself. Because of a very much narrower and longer electrode leg, it is difficult to attach the electrode to the scalp. Further, the thin and sharp electrode contact side may damage the scalp.

Third, the prior semi-dry electrode fails to control discharging amount of an electrolyte solution, so it does not stably discharge the electrolyte solution or it discharges a very small amount very slowly. Therefore, the contact impedance of the prior semi-dry electrode changes variably during a recording, so it is difficult to stably record the electroencephalogram.

Fourth, the prior semi-dry electrode has a problem of an electric short-circuit that electrolyte solutions discharged by adjacent electrodes may be mixed together. To prevent the short-circuit, it only uses a very small amount of the electrolyte solution, so the amount of the electrolyte solution is not sufficient to lower the contact impedance.

Fifth, it is difficult to fix the prior semi-dry electrode to the scalp, so the prior semi-dry electrode is shaken according to the movement of the user. The semi-dry electrode needs a reservoir for storing the electrolyte solution, so it is bigger and heavier than the wet electrode. Hence, it is influenced by the motion of the body and the shaking of the head, so it is difficult to stably record the signal.

Therefore, a new semi-dry electrode for solving the problem of the prior semi-dry electrode is required so as to conveniently record an electroencephalogram with high reliability in daily life.

The above information disclosed in this Background section is only for enhancement of understanding of the background of the invention and therefore it may contain information that does not form the prior art that is already known in this country to a person of ordinary skill in the art.

SUMMARY

The present invention has been made in an effort to provide a membrane-based semi-dry electrode for recording a brain signal by discharging an electrolyte solution through a membrane attached to a scalp, and particularly, to provide a double-membrane-based semi-dry electrode.

An exemplary embodiment of the present invention provides a semi-dry electrode for recording an electroencephalogram. The semi-dry electrode includes: an outer membrane that forms an electrode contact surface with a predetermined area contacting a scalp; an electrode body that is connected to an edge of the outer membrane and forms an internal space into which an electrolyte solution is filled; and an electrical conductor sensor that is located inside the electrode body and measures an ion current transmitted through the outer membrane. The outer membrane has a plurality of fine holes and holes that are larger than the fine holes.

The outer membrane may include a material that swells and inflates when absorbing an electrolyte solution.

The outer membrane may include a cellulose material.

The electrode body may be manufactured with a flexible material that is transformed when an external pressure is applied.

The semi-dry electrode may further include an inner membrane that is located inside the electrode body. The internal space of the electrode body may be divided by the inner membrane.

The inner membrane may have a plurality of fine holes. The inner membrane may include a material that is less transformed by the electrolyte solution than a material of the outer membrane.

The inner membrane may include a polyethersulfone material.

The semi-dry electrode may further include a short-preventing solid edge that is attached to a circumference of an outer membrane.

The short-preventing solid edge may be manufactured with a cohesive nonelectrolyte material.

When the electrode contact surface is attached to the scalp, an electrolyte solution of the electrode body may flow toward the scalp through the outer membrane according to a scalp contact pressure applied to the outer membrane to form an electrolyte layer between the scalp and the outer membrane. The electrolyte solution of the electrode body may be discharged toward the scalp by diffusion.

Another embodiment of the present invention provides a semi-dry electrode for measuring an electroencephalogram. The semi-dry electrode includes: an outer membrane having a plurality of holes that forms an electrode contact surface with a predetermined area contacting a scalp; an electrode body that is connected to an edge of the outer membrane and forms an internal space into which an electrolyte solution is filled; an inner membrane having a plurality of holes that is located inside the electrode body and divides the internal space into a catalysis space and a measuring space; a catalyst input unit that puts a catalyst toward the catalysis space; and an electrical conductor sensor that measures an ion current transmitted through the outer membrane in the measuring space of the electrode body.

When the electrode contact surface is attached to the scalp, an electrolyte solution of the electrode body may be discharged toward the scalp by diffusion. A discharging amount and a discharging speed of the electrolyte solution discharged toward the scalp through the outer membrane may be controlled by a catalyst input through the catalyst input unit.

Another embodiment of the present invention provides a semi-dry electrode for measuring an electroencephalogram. The semi-dry electrode includes: an outer membrane that forms an electrode contact surface with a predetermined area contacting a scalp, has a plurality of fine holes and holes that are larger than the fine holes, and is a material that swells and inflates when absorbing an electrolyte solution; an electrode body that is connected to an edge of the outer membrane and forms an internal space into which an electrolyte solution is filled; an inner membrane that is located inside the electrode body to divide the internal space, has a plurality of holes, and is a material that is less transformed by an electrolyte solution than the outer membrane; and an electrical conductor sensor that is located inside the electrode body and measures an ion current transmitted through the outer membrane.

When the electrode body is filled with the electrolyte solution, the outer membrane may not discharge the electrolyte solution but swells and inflates because of a surface tension of the holes in the surface.

When the outer membrane is attached to the scalp, the swelled electrode contact surface may be transformed according to the scalp shape and may be then closely attached. The outer membrane may discharge the electrolyte solution toward the scalp by an internal pressure of the electrode body that is increased by a scalp contact pressure to generate an electrolyte layer on the scalp.

After the electrolyte layer is generated, the outer membrane may discharge the electrolyte solution toward the scalp by diffusion as an internal pressure of the electrode body is in balance with an external atmospheric pressure.

The semi-dry electrode according to the exemplary embodiment may have a short electrode setup time, may solve the drawback of the wet electrode generating the defilement of the scalp caused by the electrolyte gel to thus increase the convenience of recording the electroencephalogram, and may provide low contact impedance like the wet electrode to thus increase recording performance.

DETAILED DESCRIPTION OF THE EMBODIMENTS

Figure 1:
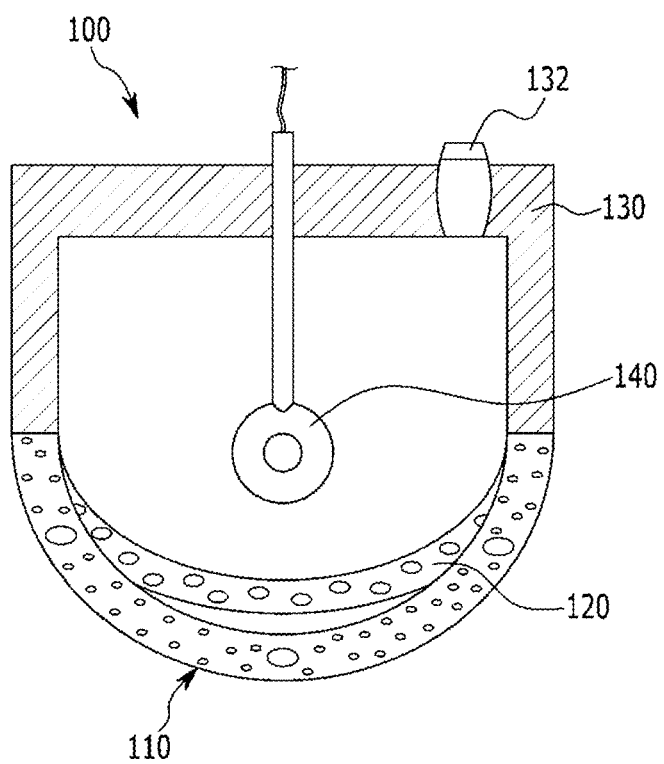
FIG. 1 is a schematic diagram illustrating a double-membrane-based semi-dry electrode according to an exemplary embodiment.

In the following detailed description, only certain exemplary embodiments of the present invention have been shown and described, simply by way of illustration. As those skilled in the art would realize, the described embodiments may be modified in various different ways, all without departing from the spirit or scope of the present invention. Accordingly, the drawings and description are to be regarded as illustrative in nature and not restrictive. Like reference numerals designate like elements throughout the specification.

Unless explicitly described to the contrary, the word "comprise" and variations such as "comprises" or "comprising" will be understood to imply the inclusion of stated elements but not the exclusion of any other elements. In addition, the terms "-er", "-or", and "module" described in the specification mean units for processing at least one function and operation, and can be implemented by hardware components or software components and combinations thereof.

FIG. 1 is a schematic diagram illustrating a double-membrane-based semi-dry electrode according to an exemplary embodiment, and is a schematic diagram illustrating a double-membrane-based semi-dry electrode swelled according to an exemplary embodiment.

Referring to FIG. 1, a semi-dry electrode 100 continuously discharges an electrolyte solution to a contacting scalp. An ion current generated by neurons in the brain is measured by an electrical conductor sensor 140 provided in the semi-dry electrode 100 through the discharged electrolyte solution. The ion current is converted into an electrical signal by the electrical conductor sensor 140, and is output as an electroencephalogram (EEG).

The semi-dry electrode 100 includes an outer membrane 110 that is an electrode contact surface with a predetermined area contacting the scalp. The semi-dry electrode 100 includes an electrode body 130 connected to an edge of the outer membrane 110 as a flexible material of which shapes are changed when a pressure is applied, and forming a storage place for storing an electrolyte solution inside thereof. The semi-dry electrode 100 includes the electrical conductor sensor 140 located inside the electrode body 130 and measuring the ion current transmitted through the outer membrane 110. The semi-dry electrode 100 may further include an inner membrane 120 located inside the electrode body 130. The semi-dry electrode 100 discharges the electrolyte solution through a double membrane structure including the outer membrane 110 and the inner membrane 120.

The outer membrane 110 is a layer of which a surface includes a plurality of fine holes and a small amount of holes with a constant size. The outer membrane 110 is made of a material that inflates according to a swelling phenomenon when it absorbs the electrolyte solution (solvent). The hole size of the outer membrane 110 may be variously designed, and for example, the outer membrane 110 may have a plurality of 0.02 μm fine holes and a small amount of 300 μm holes.

Figure 2:
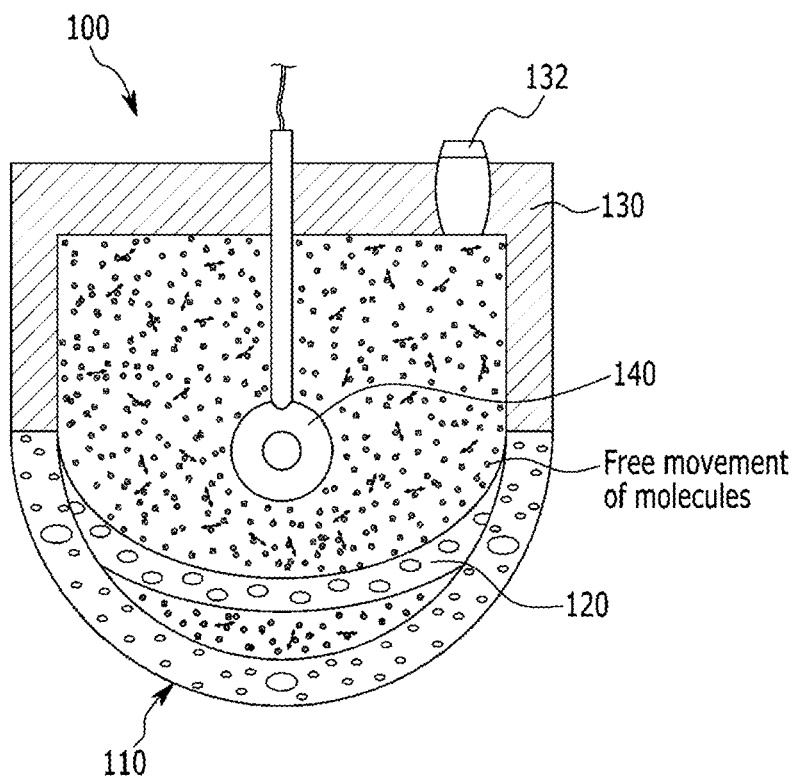
FIG. 2 is a schematic diagram illustrating a double-membrane-based semi-dry electrode swelled according to an exemplary embodiment.

The outer membrane 110 may be a layer including a cellulose material. Without being limited to the cellulose material, materials that increase in flexibility and elasticity when absorbing the electrolyte solution may be used. Referring to FIG. 2, when the electrolyte solution is filled in the semi-dry electrode 100, the outer membrane 110 is swelled by the electrolyte solution. The swelled outer membrane 110 becomes very flexible and elastic so it changes to have a soft and pliable characteristic. Therefore, the attachment of the semi-dry electrode 100 to the scalp may be increased.

In the case of a double membrane structure, the semi-dry electrode 100 further includes the inner membrane 120 inside the outer membrane 110, that is, inside the electrode body 130. The inner membrane 120 is a layer of which the surface includes a plurality of fine holes. Differing from the outer membrane 110, the inner membrane 120 is a layer of a material that is less transformed or more solid by the electrolyte solution. The hole size of the inner membrane 120 may be variously designed, for example, the inner membrane 120 may have a plurality of 0.2 μm fine holes. The inner membrane 120 may be a layer including a polyethersulfone material that quickly transmits through the electrolyte solution and has strong durability. But the material of the inner membrane 120 is not limited to the polyethersulfone material.

In addition, when the swelled outer membrane 110 contacts the scalp, the outer membrane 110 may shrink by the contact pressure between the scalp and the electrode and may be inserted into the electrode in a concave way. When the outer membrane 110 is transformed to be concave, the electrode fails to be attached to the scalp and the attachment is reduced. However, in the case of the double membrane structure, the inner membrane 120 with high durability and stiffness prevents the outer membrane 110 from being input into the electrode in a concave way by the contact pressure. As described, the inner membrane 120 maintains the shape of the outer membrane 110 to be convex when it is closely attached to the scalp, and increases the close contacting property of the electrode to the scalp. Further, the inner membrane 120 prevents the outer membrane 110 from being damaged by the rigid electrical conductor sensor 140 and maintains the electrolyte solution storage space.

The electrode body 130 has a shape such that it is connected to the edge of the outer membrane 110 to form a closed and sealed internal space, and it is manufactured of a flexible material (e.g., rubber) that is transformed when an external pressure is applied. The electrode body 130 includes an injecting hole 132 for injecting an electrolyte solution to the inside, and the electrical conductor sensor 140 for measuring an ion current transmitted through the electrolyte solution is combined. The electrolyte solution may include electrolyte ions such as sodium or chlorine. An osmotic pressure moving toward the scalp direction becomes different according to a concentration of the electrolyte solution provided in the electrode, and influences an amount of the discharged electrolyte solution.

Figure 4:
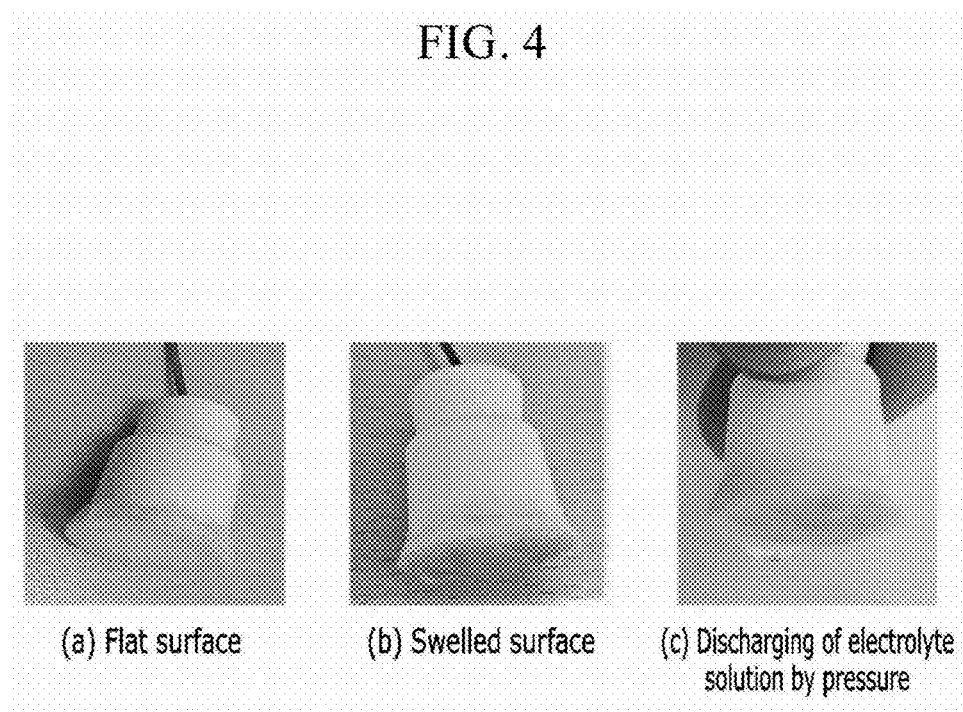
FIG. 4 is a prototype illustrating a semi-dry electrode according to an exemplary embodiment.

The shape of the electrode body 130 may be designed in various ways according to the amount of the electrolyte solution, and the shape and the size of the membrane. For example, the electrode body 130 may, as shown in FIG. 4, have a cylindrical shape or a gourd bottle shape that may apply a pressure when a user attaches the electrode to the scalp and presses the electrode in any direction. The electrode body 130 may be designed in various ways so that the user may easily grasp the electrode and attach the same, it may be stably attached to the scalp, and it may store the electrolyte solution.

The electrical conductor sensor 140 transmits a measured signal to a recording device such as a computer. The sensor may be manufactured to have various shapes.

The semi-dry electrode 100 may form a flexible contact surface in a convex shape through the double membrane structure of the outer membrane 110 and the inner membrane 120 having different characteristics, thereby increasing the close contacting property to the scalp.

The semi-dry electrode according to the present invention does not necessarily need to be a double membrane structure including an inner membrane 120. Depending on the case, the semi-dry electrode may be simply manufactured with a single membrane-based semi-dry electrode including an outer membrane 110, an electrode body 130, and an electrical conductor sensor 140.

The double membrane or single membrane structured semi-dry electrode 100 may control the amount of the electrolyte solution moving through the outer membrane 110 by a surface tension of the electrolyte solution on the outer membrane 110 and a pressure difference between the inside and the outside of the electrode. The semi-dry electrode 100 may stably discharge the electrolyte solution in the electrode to the scalp through the outer membrane 110 by a diffusion phenomenon in which molecules move freely by the osmotic pressure phenomenon. A method for a membrane-based semi-dry electrode to discharge an electrolyte solution will now be described.

Figure 3:
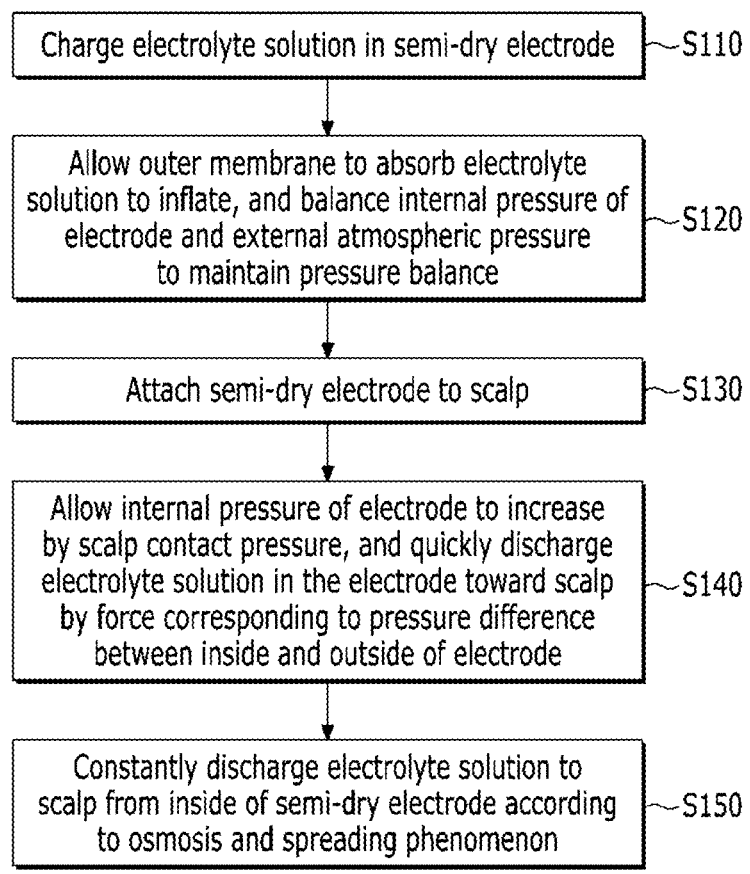
FIG. 3 is a flowchart illustrating a method for discharging an electrolyte solution of a membrane-based semi-dry electrode according to an exemplary embodiment.

FIG. 3 is a flowchart illustrating a method for discharging an electrolyte solution of a membrane-based semi-dry electrode according to an exemplary embodiment.

Referring to FIG. 3, when the electrolyte solution is injected into the injecting hole 132 of the semi-dry electrode 100, the electrolyte solution having passed through the inner membrane 120 of the semi-dry electrode 100 is blocked by the outer membrane 110, so the electrolyte solution is charged in the semi-dry electrode 100 (S110).

The outer membrane 110, as shown in FIG. 2, absorbs the electrolyte solution and inflates, and the internal pressure of the electrode and the external atmospheric pressure are balanced with each other to maintain the pressure balance (S120). In the pressure balance state, the surface tension of the electrolyte solution blocks the 300 μm holes in the outer membrane 110 to thus prevent air from being input into the electrode and prevent the electrolyte solution from flowing to the outside.

The semi-dry electrode 100 in the pressure balance state is attached to the scalp (S130). The swelled outer membrane 110 increases flexibility and elasticity, so it is freely transformed and is closely attached to the curved scalp.

Then, the internal pressure of the electrode of the swelled outer membrane 110 is increased by the scalp contact pressure to thus break the pressure balance between the inside and the outside of the electrode. The electrolyte solution in the electrode is quickly discharged toward the scalp by a force that corresponds to the pressure difference between the inside and the outside of the electrode (S140). The electrolyte solution leaked out by the scalp contact pressure forms a sufficient electrolyte layer between the scalp and the electrode to thereby steeply reduce contact impedance between the scalp and the electrode within a short time.

After this, the osmosis and the diffusion phenomenon are induced by a difference of solute concentration within the stratum corneum or sweat glands of the scalp and the electrolyte solution in the electrode. Then the electrolyte solution is constantly discharged to the scalp from the inside of the semi-dry electrode 100 (S150). Even though some of the electrolyte solution flew to the scalp dries, the electrolyte layer between the scalp and the electrode is continuously maintained by a leaked electrolyte solution according to the diffusion of the electrolyte solution. Thereby contact impedance is always in a low state.

In the case in which the measuring time is extended or a further amount of the electrolyte solution is needed depending on the scalp state, a pressure is applied to the outside of the semi-dry electrode 100 (e.g., the semi-dry electrode is pushed by a hand) to increase the pressure provided inside the electrode. Then the electrolyte solution inside the electrode quickly flows to the scalp by the pressure applied to the inside of the electrode.

In summary, regarding the semi-dry electrode 100, the outer membrane 110 having a plurality of fine holes and a plurality of holes lager than the fine hole, holds the electrolyte solution by the surface tension of the holes, then the electrolyte solution does not discharged. As the scalp contact pressure applied into the electrode when is attached to the scalp or the external pressure applied to the electrode body 130, internal pressure of the electrode of the semi-dry electrode 100 increases. Then according to pressure difference, the electrolyte solution in the electrode quickly flows through the outer membrane 110. The contact impedance between the scalp and the electrode gets lower by the electrolyte solution discharged in this way. Further, according to the diffusion phenomenon in which the molecules freely move according to a concentration difference of the solute, the semi-dry electrode 100 allows the electrolyte solution in the electrode to continuously flow to the scalp through the outer membrane 110. The contact impedance between the scalp and the electrode is maintained in low impedance by the electrolyte solution having moved according to the diffusion.

FIG. 4 is a prototype illustrating a semi-dry electrode according to an exemplary embodiment.

Referring to FIG. 4 (a), before the semi-dry electrode 100 is charged with the electrolyte solution, the semi-dry electrode 100 is flat since the outer membrane 110 does not swell.

Referring to FIG. 4 (b), after the semi-dry electrode 100 is charged with the electrolyte solution, the outer membrane 110 absorbs the electrolyte solution so that the outer membrane 110 swells and inflates. In this instance, the surface tension on the 300 μm holes existing in the outer membrane 110 holds the electrolyte solution, and so the electrolyte solution does not come out.

Referring to FIG. 4 (c), when the semi-dry electrode 100 is pressed, the pressure provided inside the electrode increases, so the electrolyte solution in the electrode comes out by a force that corresponds to the pressure difference between the inside and the outside of the electrode. In a like manner, when the semi-dry electrode 100 is attached to the scalp, the pressure provided inside the electrode increases by the scalp contact, so the electrolyte solution comes out of the inside of the electrode by the force that corresponds to the pressure difference between the inside and the outside of the electrode.

Figure 5:
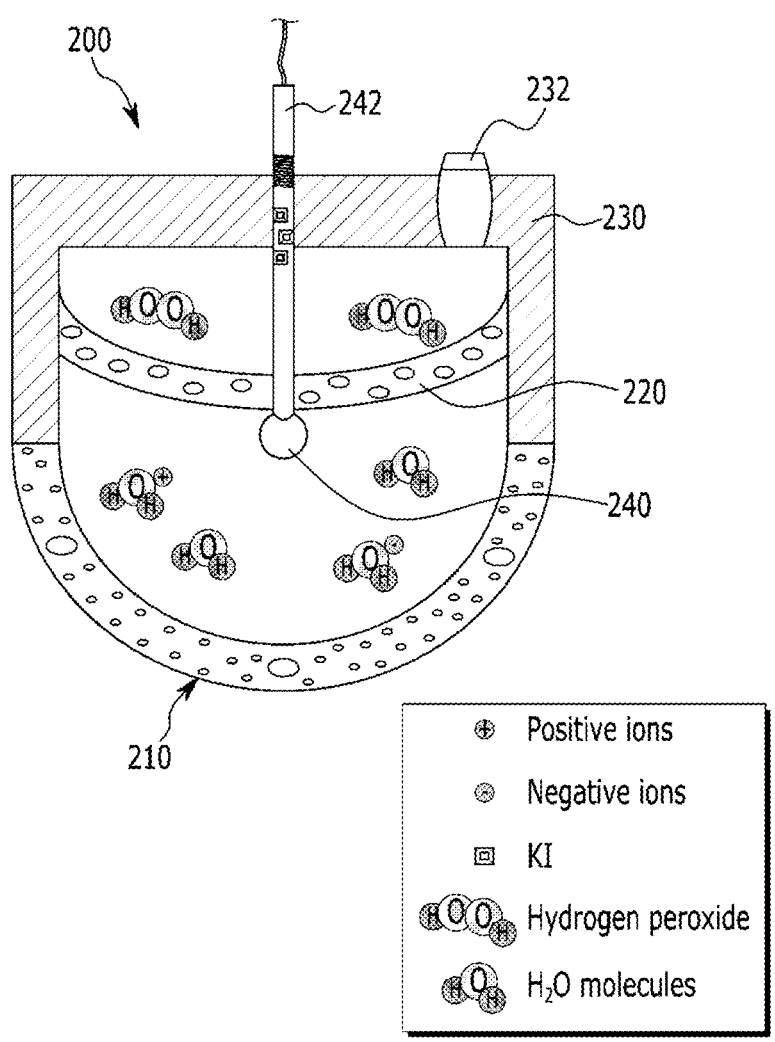
FIG. 5 is a schematic diagram illustrating a catalyst-based semi-dry electrode according to another exemplary embodiment.
Figure 6:
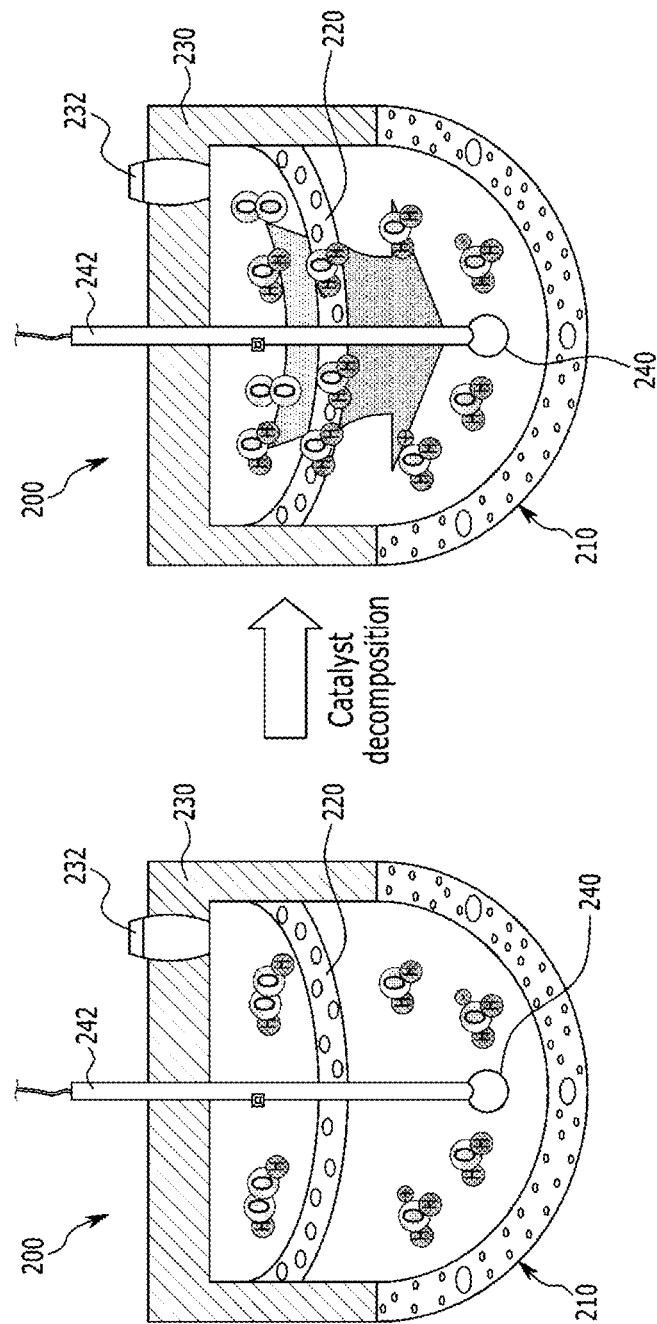
FIG. 6 is a schematic diagram illustrating a method for discharging an electrolyte solution of a catalyst-based semi-dry electrode according to another exemplary embodiment.

FIG. 5 is a schematic diagram illustrating a catalyst-based semi-dry electrode according to another exemplary embodiment, and FIG. 6 is a schematic diagram illustrating a method for discharging an electrolyte solution of a catalyst-based semi-dry electrode according to another exemplary embodiment.

Referring to FIG. 5, the semi-dry electrode 200 controls the diffusion of the electrolyte solution by using catalyst decomposition inside the electrode. The semi-dry electrode 200 includes an outer membrane 210 that is an electrode contact surface with a predetermined area contacting the scalp, an electrode body 230 including an edge to which the outer membrane 210 is connected to form a storage unit for storing the electrolyte solution, and an electrical conductor sensor 240 located inside the electrode body 230. The semi-dry electrode 200 further includes an inner membrane 220 for forming a catalysis space inside the electrode body 230. The inner membrane 220 is located inside the electrode body 230 to divide the internal space into a catalysis space and a measuring space. The electrical conductor sensor 240 measures the ion current transmitted through the outer membrane in the measuring space.

The catalyst is put into the catalysis space formed by the inner membrane 220 to control an amount of the electrolyte solution discharged to the scalp and a discharging rate. The catalyst may be put into the catalysis space through an additional catalyst input unit (not shown) connected to the inside of the electrode body 230 or an electrolyte solution injecting hole 232. In another way, the catalyst may be put into the catalysis space formed in a supporter 242 of the electrical conductor sensor 240.

The outer membrane 210 and the inner membrane 220 are layers of which the surfaces have a plurality of fine holes. For example, the outer membrane 210 and the inner membrane 220 may be semi-permeable membranes having a plurality of 0.02 μm fine holes. The semi-dry electrode 200 may not use the surface tension and the pressure difference between the inside and the outside of the electrode but use the diffusion phenomenon controlled by the catalyst for discharging the electrolyte solution. Therefore the semi-dry electrode 200 may use a semi-permeable membrane through which water molecules are transmitted. The outer membrane 210 may be a layer including a cellulose material so as to increase the attachment to the scalp. The inner membrane 220 may be a layer with a material that has high durability, is particularly strong against thermal energy of the catalysis, and has low thermal conductivity.

The electrode body 230 has a shape such that it is connected to an edge of the outer membrane 210 to form a closed and sealed internal space, and a catalysis space is formed by the inner membrane 220. The semi-dry electrode 200 does not use the pressure difference between the inside and the outside of the electrode but uses the diffusion phenomenon controlled by the catalyst, so the electrode body 230 is manufactured with a material that has high durability, is particularly strong against the thermal energy of the catalysis, and has low thermal conductivity.

The electrical conductor sensor 240 is located inside the electrode body 230, measures the ion current transmitted though the outer membrane 210, and transmits a measured signal to a recording device such as a computer. The electrical conductor sensor 240 may be located between the outer membrane 210 and the inner membrane 220. The supporter 242 of the electrical conductor sensor 240 may form a path for inputting a catalyst to the catalysis space inside the supporter 242. The supporter 242 may include a structure for controlling the amount of the catalyst, and for example, it may have a bolt-shaped structure.

Referring to FIG. 6, an electrolyte solution is injected into the injecting hole 232 of the semi-dry electrode 200, and the catalyst is input to the catalysis space of the semi-dry electrode 200. The amount of the catalyst may be determined according to the diffusion speed/rate (discharging speed) of the electrolyte solution and the scalp state.

The spreading speed of the electrolyte solution is proportional to the free moving speed of the molecules, and the free moving speed of the molecules changes by the concentration, the temperature, and the pressure according to the osmotic pressure formula of Equation 1 of the electrolyte solution. Therefore, when the concentration, the temperature, and the pressure increase, the osmotic pressure increases by the fast free moving of the molecules of the electrolyte solution and the electrolyte solution is quickly discharged. In Equation 1, $\pi$ is the osmotic pressure, i is the van't Hoff factor, M is the molarity, R is the gas constant, and T is the absolute temperature.

$$\pi = iMRT \quad \text{(Equation 1)}$$

A decomposition of the hydrogen peroxide ($H_2O_2$) is expressed in Equation 2. As can be known from the hydrogen peroxide decomposition, the water molecules, oxygen, and thermal energy generated by the hydrogen peroxide decomposition increases the concentration, pressure, and temperature of the electrolyte solution to accelerate the molecular movement of the electrolyte solution.

$$2H_2O_2 \rightarrow 2H_2O + O_2 + \text{thermal energy} \quad \text{(Equation 2)}$$

Hence, the molecular movement is accelerated by adding a hydrogen peroxide decomposition structure to the semi-dry electrode 200, so the speed of discharging the electrolyte solution to the outer membrane 210 increases. When potassium iodide (KI) that is a positive catalyst is input to the catalysis space, activation energy of the hydrogen peroxide decomposition is reduced to accelerate the decomposition speed and the molecular movement becomes faster. The decomposition speed depends on the inputting time and the inputting amount of the catalyst. The supporter 242 or an additional catalyst input unit (not shown) may include a structure for controlling the amount of the catalyst.

As described, the semi-dry electrode 200 discharges the electrolyte solution by using the diffusion phenomenon and controls the molecule moving speed according to the catalyst decomposition of the hydrogen peroxide. Thereby the semi-dry electrode 200 stably discharges the electrolyte solution and controls the discharging speed of the electrolyte solution.

Figure 7:
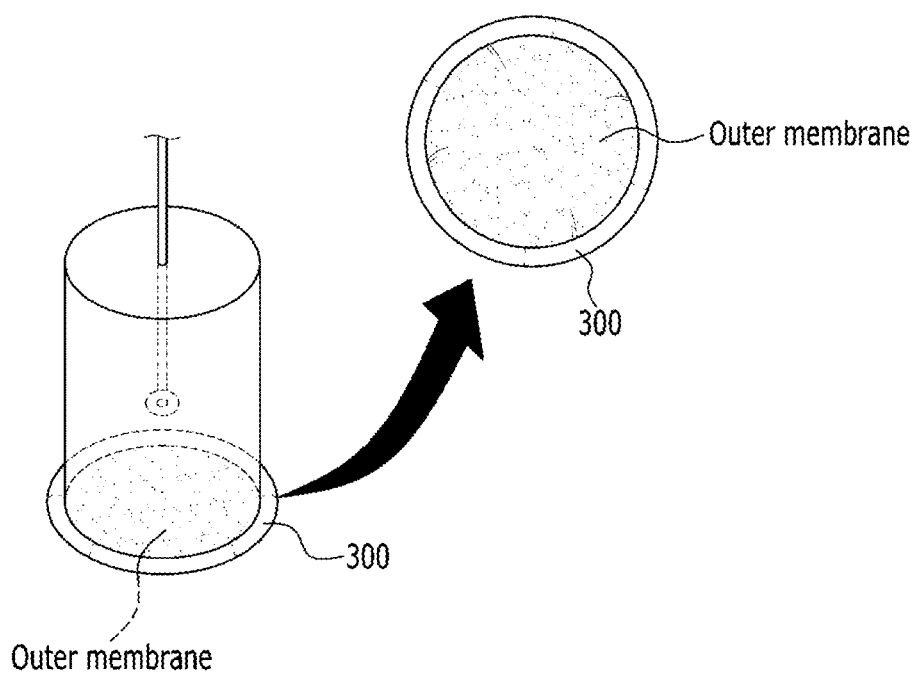
FIG. 7 is a schematic diagram illustrating a semi-dry electrode including a short-preventing edge according to an exemplary embodiment.

FIG. 7 is a schematic diagram illustrating a semi-dry electrode including a short-preventing edge according to an exemplary embodiment.

Referring to FIG. 7, a short-preventing solid edge 300 may be attached to the semi-dry electrode 100 or an outer membrane circumference that is an electrode contact surface of the semi-dry electrode 200. The solid edge 300 is a cohesive nonelectrolyte material to increase the attachment to the scalp compared to the case in which the outer membrane is only attached. The solid edge 300 may prevent the electrical short phenomenon in which the electrolyte solution leaked out from a neighboring electrode is mixed. In FIG. 7, the internal semi-dry structure is simplified so as to describe the solid edge 300.

Figure 8:
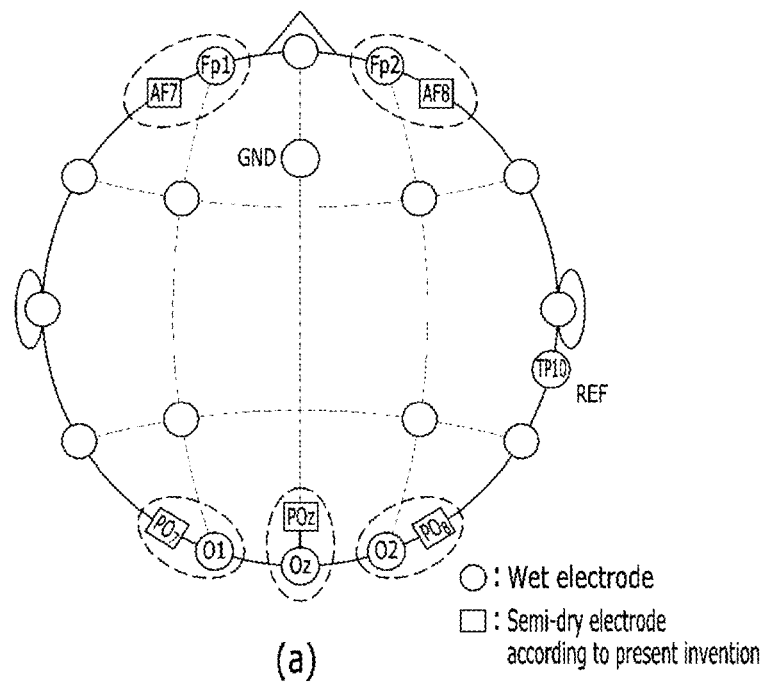
FIG. 8 shows a graph for comparing results of recording contact impedance of a wet electrode and a semi-dry electrode according to the present invention.
Figure 9:
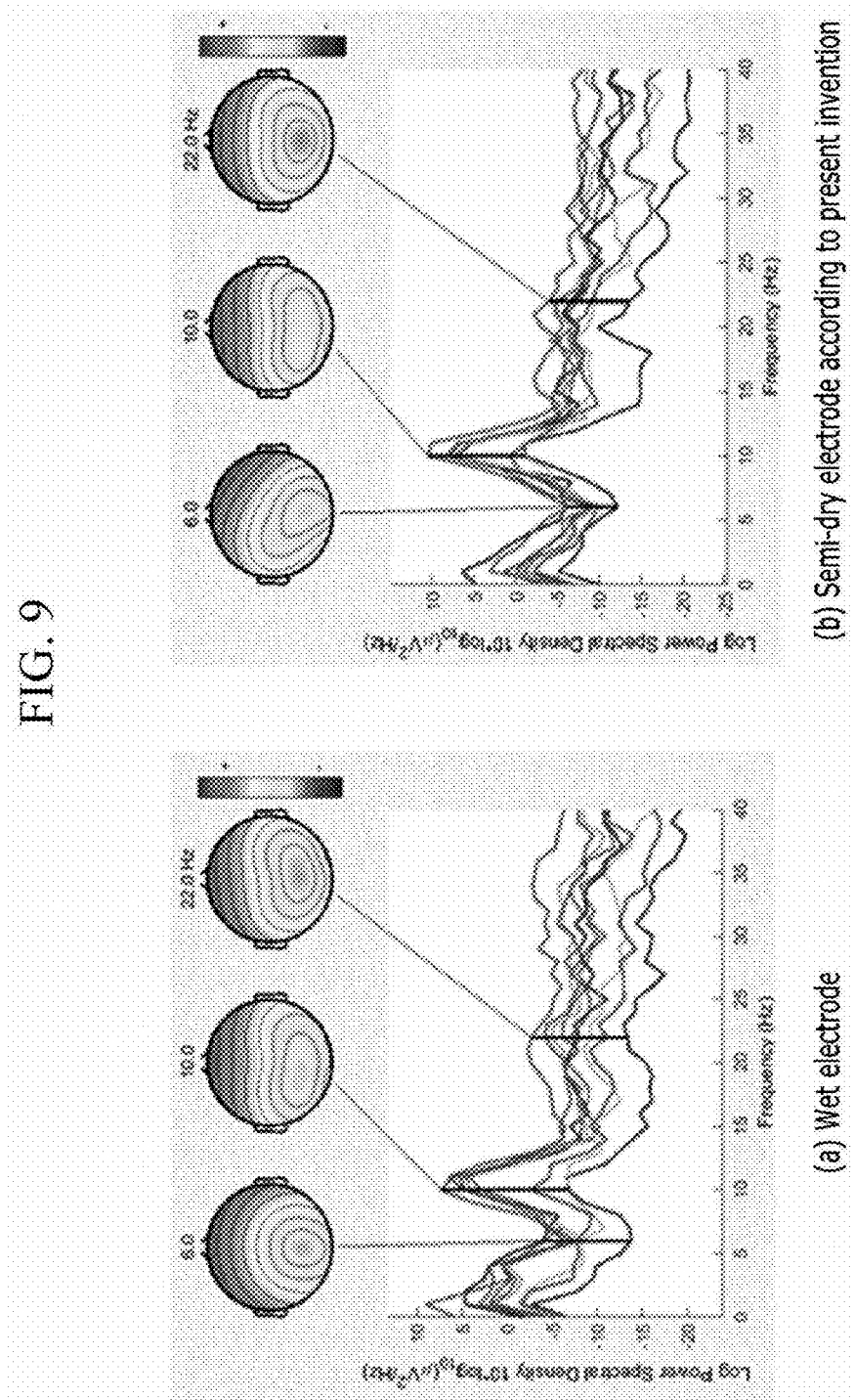
FIG. 9 shows a graph for comparing similarities of measured electroencephalograms of a wet electrode and a semi-dry electrode according to the present invention.

FIG. 8 shows a graph for comparing results of recording contact impedance of a wet electrode and a semi-dry electrode according to the present invention, and FIG. 9 shows a graph for comparing similarities of measured electroencephalograms of a wet electrode and a semi-dry electrode according to the present invention.

As shown in FIG. 8 (*a*), the respective membrane-based semi-dry electrodes (square positions) according to the present invention and the wet electrodes (circular positions) are attached to the adjacent electroencephalogram channel positions, and contact impedance is measured while an electroencephalogram is produced. Here, a ground electrode and a reference electrode are semi-dry electrodes.

Impedance of the semi-dry electrode and the wet electrode are checked for an hour during a performance test. Next, the electroencephalograms are acquired. It is used to compare and analyze electroencephalograms of the semi-dry electrode and the wet electrode. In this instance, changes of the electroencephalogram of a rhythm are checked for respective channels through a power spectrum analysis. The electroencephalogram of a rhythm is generated when a user closes eyes and is generally used for a performance comparison test of a new-type electrode.

Referring to FIG. 8 (*b*), the membrane-based semi-dry electrode according to the present invention shows a similar impedance value to that of the wet electrode at the adjacent channel position. Particularly, while impedance of the conventional semi-dry electrode is 30-80 kΩ that is higher than that of the wet electrode, the semi-dry electrode according to the present invention shows the measured impedance value that is equal to or less than 10 kΩ that corresponds to the level of the wet electrode.

Referring to FIG. 9 (a), the graph of the wet electrode indicates activation degrees of a scalp map for respective a rhythms (8-13 Hz) generated when the eyes are closed and respective frequency. Referring to FIG. 9 (b), the graph of the semi-dry electrode according to the present invention shows activation degrees of a scalp map for respective a rhythms (8-13 Hz) generated when the eyes are closed and respective frequencies.

In comparison of graphs of (a) and (b), according to a power spectrum analysis on the a rhythm (8-13 Hz), the electroencephalogram of the semi-dry electrode according to the present invention shows similar results to the electroencephalogram of the wet electrode. Similar activation forms are shown at similar positions on the respective scalp maps.

Therefore, we know that the semi-dry electrode according to the present invention provides performance close to that of the wet electrode.

Figure 10:
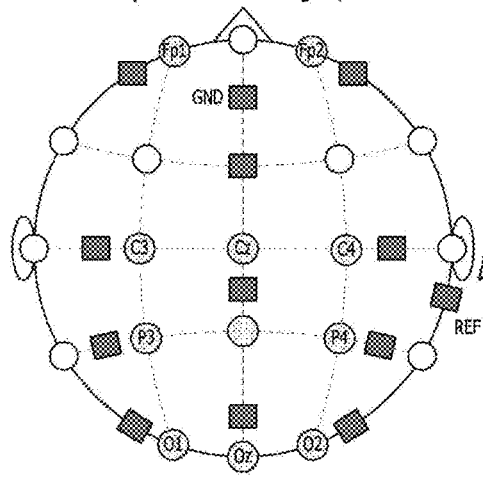
FIG. 10 shows changes of contact impedance of a wet electrode and a semi-dry electrode according to the present invention with respect to time.
Figure 10:
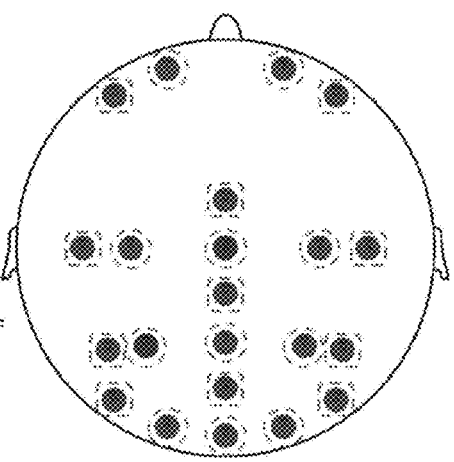
Figure 10:
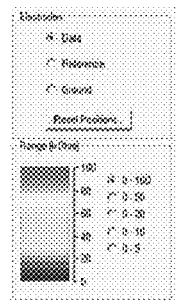
Figure 10:
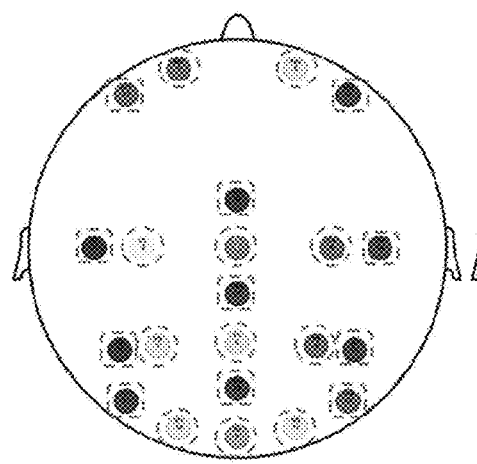
Figure 10:
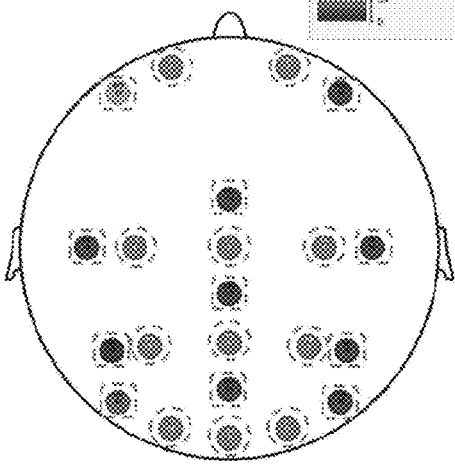

FIG. 10 shows changes of contact impedance of a wet electrode and a semi-dry electrode according to the present invention with respect to time.

As shown in FIG. 10 (a), the respective membrane-based semi-dry electrodes (square positions) according to the present invention and the wet electrodes (circle positions) are attached to the adjacent electroencephalogram channel positions, and contact impedance is measured while an electroencephalogram is produced. Here, a ground electrode and a reference electrode are semi-dry electrodes. Impedance of the semi-dry electrode and the wet electrode are checked for an hour during a performance test.

Referring to FIG. 10 (b), the semi-dry electrodes according to the present invention and the wet electrodes are respectively attached to the channel positions for the electroencephalogram, and the impedance measured after an hour is shown to be equal to or less than 10 kΩ.

Referring to FIG. 10 (c), it shows the changes of impedance measured at the semi-dry electrodes according to the present invention and the wet electrodes after five hours from the attachment to the scalp. It is found that the impedances of the channels of the semi-dry electrodes are maintained. But as a gel attached to the wet electrode gets dried, the impedances of the wet electrodes generally increase, and particularly the impedances of some channels attached around a top of a head increases highly.

Referring to FIG. 10 (d), it shows the changes of impedance measured at the semi-dry electrodes according to the present invention and the wet electrodes after seven hours from the attachment to the scalp. The impedances of the semi-dry electrodes are maintained to be similar to the initial impedances on the entire channels, but the impedances of the wet electrode has increased to be about 100 kΩ on the entire channel since the gel has dried.

When the impedance measured at some channels increases through the long-time measurement, the user may lower the impedance of the corresponding channel to the initial impedance in a low level by a simple operation of pressing the semi-dry electrode 100 and thereby discharging the electrolyte solution to the scalp.

In another way, the user may lower the impedance of the corresponding channel to the initial impedance in a low level by inputting a catalyst to the semi-dry electrode 200 and thereby increasing discharging of the electrolyte solution to the scalp.

Figure 11:
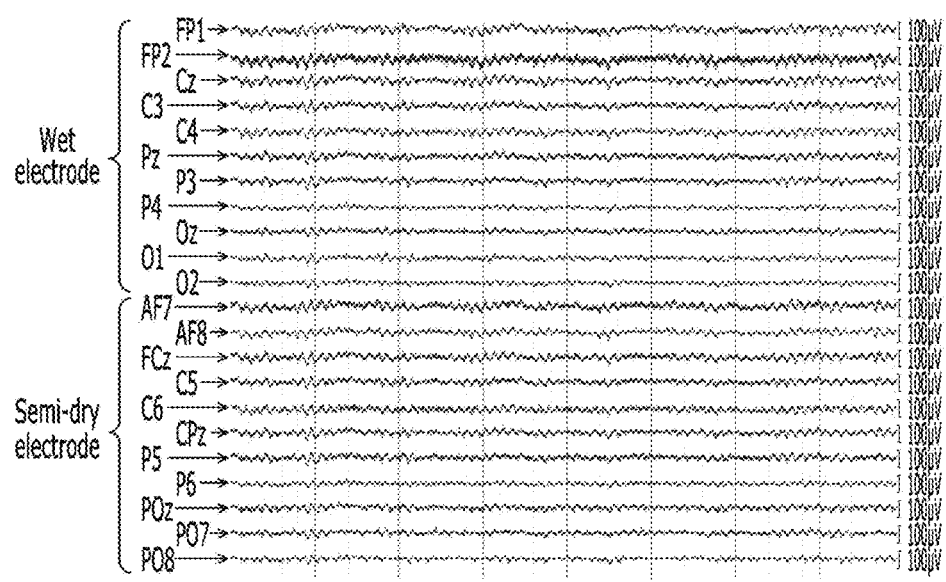
FIG. 11 shows changes of electroencephalograms of a wet electrode and a semi-dry electrode according to the present invention with respect to time.
Figure 11:
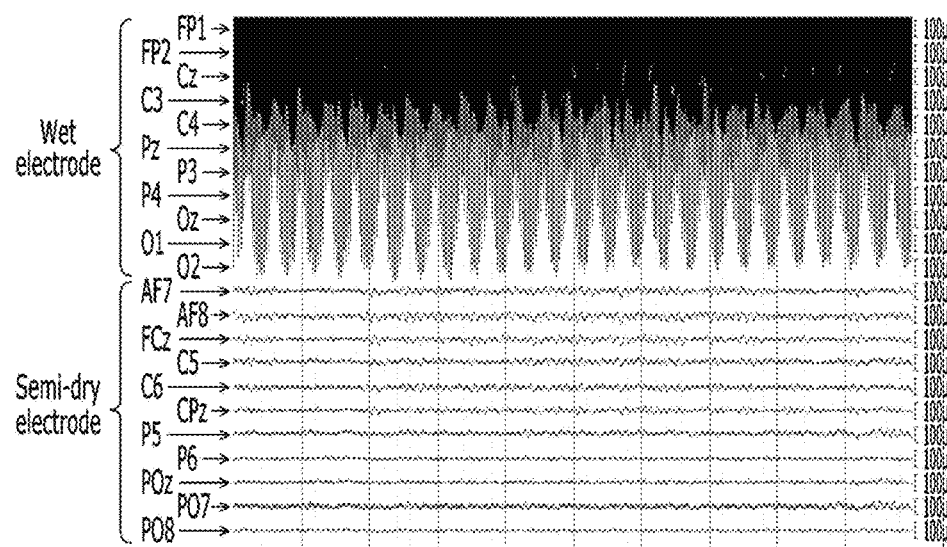

FIG. 11 shows changes of electroencephalograms of a wet electrode and a semi-dry electrode according to the present invention with respect to time.

Referring to FIG. 11 (a), it shows electroencephalogram data output by a wet electrode and a semi-dry electrode according to the present invention at an earlier stage of measurement.

Referring to FIG. 11 (b), it shows electroencephalogram data output after eight hours have passed when a wet electrode and a semi-dry electrode according to the present invention are attached to a scalp. The wet electrode has a merit of low contact impedance because of an electrolyte gel, but when the electrolyte gel between the scalp and the electrode dries, electroencephalogram measuring efficiency is degraded because of noise. However, the electrolyte solution is consecutively came out and discharged to the scalp, so the semi-dry electrode according to the present invention provides the same measured result as the initial stage when the time has passed.

Table 1 expresses results of comparing impedance of a semi-dry electrode according to the present invention, a wet electrode (M. A. L. Gordo), and conventional semi-dry electrodes, impedance provided after eight hours, and an SNR. According to Table 1, it is found that impedance of the semi-dry electrode according to the present invention is provided to be close to that of the wet electrode, the impedance change is less when time has passed, and the SNR is a little higher than other semi-dry electrodes and is similar to that of the wet electrode.

TABLE 1

| Source | Type | Impedance (KΩ@10 Hz) | Long time impedance during 8 hours | SNR (SSVEP) |
|---|---|---|---|---|
| M. A. L. Gordo et al. 2014 | Wet | 5-10 kΩ | 100 kΩ after gel drying | 25 ± 3 dB |
| A. R. Mota et al. 2013 | Semi-dry | 40 kΩ | — | — |
| H. L. Peng et al. 2016 | Semi-dry | 23 kΩ | 33 kΩ | 24.4 dB |
| G. Li et al. 2016 | Semi-dry | 44.4 ± 16.9 kΩ | 64.4 ± 16.9 kΩ | 21 ± 3 dB |
| P. Pedrosa et al. 2017 | Semi-dry | 37 ± 11 kΩ | 37 ± 11 kΩ | — |
| X. Xing et al. 2018 | Semi-dry | 12.1 ± 1.3 kΩ | 26.7 ± 2.3 kΩ | 23 ± 3.5 dB |
| Semi-dry electrode according to the present invention | Semi-dry | 8.3 ± 4.0 kΩ | 7.6 ± 3.7 kΩ | 24.9 ± 4.5 dB |

As described, the semi-dry electrode according to an exemplary embodiment stably discharges the electrolyte solution through the membrane closely attached to the scalp to reduce the contact impedance of the scalp and the electrode, and it stably discharges the electrolyte solution to maintain low contact impedance when the measuring time increases, thereby measuring the high-quality brain signal.

The above-described embodiments can be realized through a program for realizing functions corresponding to the configuration of the embodiments or a recording medium for recording the program, in addition to through the above-described device and/or method. In addition, the above-described method may be realized by a recording medium including instructions that are readable by a computer.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A semi-dry electrode for recording an electroencephalogram, comprising:
    an outer membrane that forms an electrode contact surface with a predetermined area contacting a scalp;
    an electrode body that is connected to an edge of the outer membrane and forms an internal space into which an electrolyte solution is filled; and
    an electrical conductor sensor that is located within the internal space and measures an ion current transmitted through the outer membrane,
    wherein the outer membrane has a plurality of fine holes and holes that are larger than the fine holes.

2. The semi-dry electrode of claim 1, wherein
    the outer membrane includes a material that swells and inflates when absorbing the electrolyte solution.

3. The semi-dry electrode of claim 2, wherein
    the outer membrane includes a cellulose material.

4. The semi-dry electrode of claim 1, wherein
    the electrode body includes a flexible material adaptable to transformation when an external pressure is applied to the electrode body.

5. The semi-dry electrode of claim 1, further comprising an inner membrane that is located inside the internal space,
    and the internal space is partitioned by the inner membrane.

6. The semi-dry electrode of claim 5, wherein
    the inner membrane has fine holes, and the inner membrane includes a material adaptable to transformation, and the outer membrane includes a material adapted to transformation, wherein the outer membrane material is transformed to a greater extent than that of the inner membrane material by the electrolyte solution.

7. The semi-dry electrode of claim 5, wherein
    the inner membrane includes a polyethersulfone material.

8. The semi-dry electrode of claim 1, further comprising a short-preventing solid edge attached to a circumference of the outer membrane.

9. The semi-dry electrode of claim 8, wherein
    the short-preventing solid edge is formed from a cohesive nonelectrolyte material.

10. The semi-dry electrode of claim 1, wherein
    the electrode contact surface is configured to contact the scalp, when a pressure is applied to the outer membrane and the electrolyte solution within the internal space is adapted to flow towards the scalp by diffusion through the outer membrane to form an electrolyte layer between the scalp and the outer membrane.

11. A semi-dry electrode for measuring an electroencephalogram, comprising:
    an outer membrane having a plurality of holes that forms an electrode contact surface with a predetermined area adapted to contact a scalp;
    an electrode body that is connected to an edge of the outer membrane, the electrode body forming an internal space that is filled with an electrolyte solution;
    an inner membrane having a plurality of holes, the inner membrane located within the electrode body and partitions the internal space into a catalysis space and a measuring space;
    a catalyst input unit providing a catalyst for the catalysis space; and
    an electrical conductor sensor that measures an ion current transmitted through the outer membrane in the measuring space of the electrode body.

12. The semi-dry electrode of claim 11, wherein
    when the electrode contact surface is configured to attach to the scalp, the electrolyte solution is adapted to discharge from the electrode body toward the scalp by diffusion, wherein a discharging amount and a discharging speed of the electrolyte solution toward the scalp through the outer membrane are controlled by the catalyst input unit.

13. A semi-dry electrode for measuring an electroencephalogram, comprising:
    an outer membrane that forms an electrode contact surface with a predetermined area adapted to contact a scalp, the outer membrane including a plurality of fine holes and holes that are larger than the fine holes, and a material adapted for transformation by an electrolyte solution, and that swells and inflates when absorbing an electrolyte solution;
    an electrode body that is connected to an edge of the outer membrane and forms an internal space filled with the electrolyte solution;
    an inner membrane that is located within the electrode body and partitions the internal space, the inner membrane including a plurality of holes, and a material adapted for transformation to an extent less than the outer membrane by the electrolyte solution; and
    an electrical conductor sensor that is located within the internal space and measures an ion current transmitted through the outer membrane.

14. The semi-dry electrode of claim 13, wherein
    surface tension of the holes on the electrode contact surface causes swelling and inflating of the electrode contact surface and prevents discharge of electrolyte solution when the electrode body is filled with the electrolyte solution.

15. The semi-dry electrode of claim 14, wherein
    the swollen and inflated outer membrane is adapted to discharge the electrolyte solution toward the scalp to generate an electrolyte layer on the scalp when the internal pressure of the electrode body causes an increase in scalp contact pressure as the outer membrane attaches and conforms to the scalp.

16. The semi-dry electrode of claim 15, wherein
    the outer membrane is adapted to discharge the electrolyte solution toward the scalp by diffusion to maintain a balance between an internal pressure of the electrode body and the external atmospheric pressure.

* * * * *